(12) United States Patent
Rachlin et al.

(10) Patent No.: US 12,070,189 B2
(45) Date of Patent: Aug. 27, 2024

(54) TETHERED ENDOSCOPE

(71) Applicants: Daniel Rachlin, San Jose, CA (US); Jacques Van Dam, Los Angeles, CA (US); Venkata Vishnu Gurukula, Mountain View, CA (US)

(72) Inventors: Daniel Rachlin, San Jose, CA (US); Jacques Van Dam, Los Angeles, CA (US); Venkata Vishnu Gurukula, Mountain View, CA (US)

( * ) Notice: Subject to any disclaimer, the term of this patent is extended or adjusted under 35 U.S.C. 154(b) by 0 days.

(21) Appl. No.: 16/716,009

(22) Filed: Dec. 16, 2019

(65) Prior Publication Data
US 2020/0390320 A1 Dec. 17, 2020

Related U.S. Application Data

(63) Continuation of application No. 14/684,061, filed on Apr. 10, 2015, now abandoned.

(60) Provisional application No. 61/977,798, filed on Apr. 10, 2014.

(51) Int. Cl.
| | |
|---|---|
| *A61B 1/00* | (2006.01) |
| *A61B 1/04* | (2006.01) |
| *A61B 1/05* | (2006.01) |
| *A61B 1/06* | (2006.01) |
| *A61B 1/07* | (2006.01) |
| *A61B 10/02* | (2006.01) |

(52) U.S. Cl.
CPC ...... *A61B 1/00147* (2013.01); *A61B 1/00018* (2013.01); *A61B 1/00114* (2013.01); *A61B 1/041* (2013.01); *A61B 1/051* (2013.01); *A61B 1/0684* (2013.01); *A61B 1/07* (2013.01); *A61B 10/02* (2013.01)

(58) Field of Classification Search
CPC ...... A61B 1/041; A61B 1/0607; A61B 1/0646
See application file for complete search history.

(56) References Cited

U.S. PATENT DOCUMENTS

| | | | | |
|---|---|---|---|---|
| 7,116,352 | B2 * | 10/2006 | Yaron | H04N 13/257 348/45 |
| 9,125,588 | B2 * | 9/2015 | Parks | A61B 1/00147 |
| 2006/0004256 | A1 * | 1/2006 | Gilad | A61B 1/041 600/160 |
| 2007/0118013 | A1 * | 5/2007 | Miyagi | A61B 1/07 600/129 |
| 2007/0299309 | A1 * | 12/2007 | Seibel | A61B 1/0638 600/117 |
| 2008/0177141 | A1 * | 7/2008 | Wu | A61B 1/00147 600/112 |
| 2010/0137686 | A1 * | 6/2010 | Meron | A61B 1/00149 600/118 |

(Continued)

*Primary Examiner* — Alexandra L Newton
(74) *Attorney, Agent, or Firm* — Moser Taboada

(57) ABSTRACT

An endoscope with flexible cable is described having a first set of means to facilitate travel of an imaging capsule down the esophagus, a second set of means to enable proper orientation and optical clarity of the capsule, and a third set of means to enable ease in retrieval of the device. In most embodiments, there is an overlap of these sets of means, the combination of which assures optimal exam effectiveness while maintaining a high degree of patient comfort. The endoscope can target low cost, high volume screening for diseases of the upper digestive tract.

27 Claims, 20 Drawing Sheets

(56) References Cited

U.S. PATENT DOCUMENTS

| | | | |
|---|---|---|---|
| 2012/0101331 A1* | 4/2012 | Gilad | A61B 1/00147 600/114 |
| 2014/0243598 A1* | 8/2014 | Genier | A61B 1/00147 600/114 |
| 2014/0343361 A1* | 11/2014 | Salman | A61B 1/0014 600/125 |

* cited by examiner 1555   1557

1559

TETHERED ENDOSCOPE

FIELD OF THE INVENTION

Diagnostic endoscopy, especially of the esophagus, is the primary field of the invention.

BACKGROUND

Endoscopes are typically semi-rigid devices that are both pushed and pulled through structures such as the esophagus. A specialization includes devices that cannot be pushed and only pulled, so called "tethered" endoscopes, through which pull forces are exerted and electrical signals flow via a thin flexible cable, or tether. These devices allow for some degree of positional control by the clinician, while avoiding the discomforting effects of rigid or large diameter cables.

There are several major areas of concern with respect to creating an esophageal imaging device that can be used to serve a broad population during, for example, routine visits to a primary care physician's office. These factors have been underappreciated in the prior art. Each of the following is of importance: 1) speed of exam; 2) patient comfort including the elimination of anxiety associated with passage of the device from the mouth and down the throat; 3) ability to optimize the view, especially of the lower anatomy; and 4) avoidance of discomfort induced by retrieving the device. An additional factor is compatibility with a low cost and single use (disposable) design.

Current approaches fail to meet the requirements for serving a broad population for diagnostic screening. For example, capsule endoscopy, which involves swallowing a pill-shaped device that captures and transmits images wirelessly, avoids the discomfort associated with a tether, but encounters significant challenges in assuring that the desired view of the esophagus is captured. These devices have no mechanically-coupled external means of control, and they make only a single pass through the anatomy of interest—there may be no "second chance." There are very limited means to adapt the device to conditions such as poor alignment or positioning. A tether line could provide some of the needed control for a capsule endoscope, but pulling out these bulky devices is likely to be problematic.

In the case of one prior device, mechanical means are described to release an imaging device from a tether. Using a tether in combination with a battery powered wireless device yields an unduly expensive solution, as a tether can easily provide the cabling needed for power and signal transmission. Capsule endoscopes are therefore expensive and, in at least one reported study, the protocol required for their use involves considerable effort to create the optimal imaging conditions.

Another area of development has been trans-nasal endoscopes. These endoscopes, since they are pushed, need to have a relatively stiff cable and therefore yield greater opportunity for discomfort when passing down the throat, as compared to having a thin flexible tether cable. They require a moderate level of skill and commensurate training. Sedative and topical anesthetic may be required. The trans-nasal endoscope has not achieved acceptance as a widely used screening tool.

Video cameras for medical purposes are available from certain manufacturers wherein the diameter of both cable and capsule is in the neighborhood of one millimeter. These devices, by themselves, they lack essential features. Very small devices cannot be swallowed easily, especially when tethered with a flexible cable. Once swallowed, they are too light and narrow to be propelled through the esophagus unless they possess a cable that allows them to be pushed.

Other prior art devices described in patent publications include the following.

U.S. Patent Application 20090286237: Cytosponge™ is a device consisting of a sponge tethered to a string. It includes a water soluble capsule such as gelatin. The device can be swallowed like a pill, and when retrieved, it accumulates within its pores cells that can be analyzed for biomarkers or other properties so as to indicate the presence of conditions such as Barrett's Syndrome.

U.S. Pat. Nos. 7,555,333 and 8,396,535: The scanning fiber endoscope uses a laser light and a mechanically scanned single mode fiber to acquire raster data from the field of view. The design of such a device allows for a very small diameter comparable to what is offered by the tiny cameras previously mentioned.

Other prior art concerns coatings and edible substances. In the medical device field, there is an abundance of materials and surface coatings that are low friction. Some are water-based such as hydrogels; others are not, such as various silicone formulations.

Edible gel-like substances include agar, gelatin and other hydrocolloids. Adding xylitol to agar is known to substantially increase its elasticity.

DESCRIPTION OF THE DRAWING FIGURES

The present invention may be further understood from the following detailed description in conjunction with the appended drawing figures. In the drawing.

Figure 12:
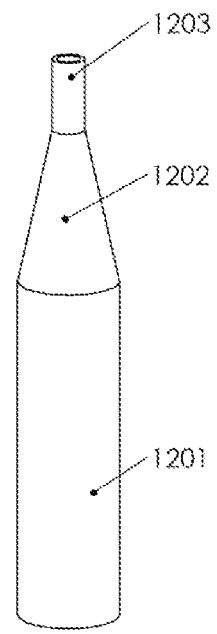
Figure 12:
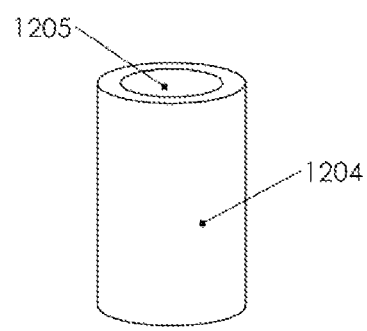
Figure 12:
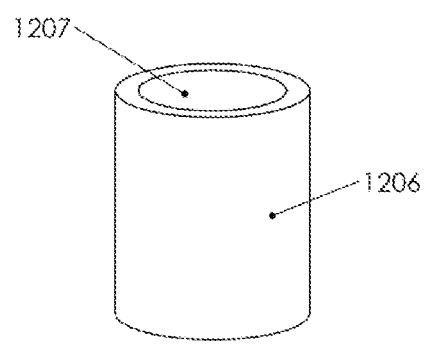

FIG. 12 shows one form of a composite sleeve structure in which an outer sleeve slips over an inner sleeve. The inner sleeve slips over an imaging capsule. Locking mechanisms are not shown.

Figure 13:
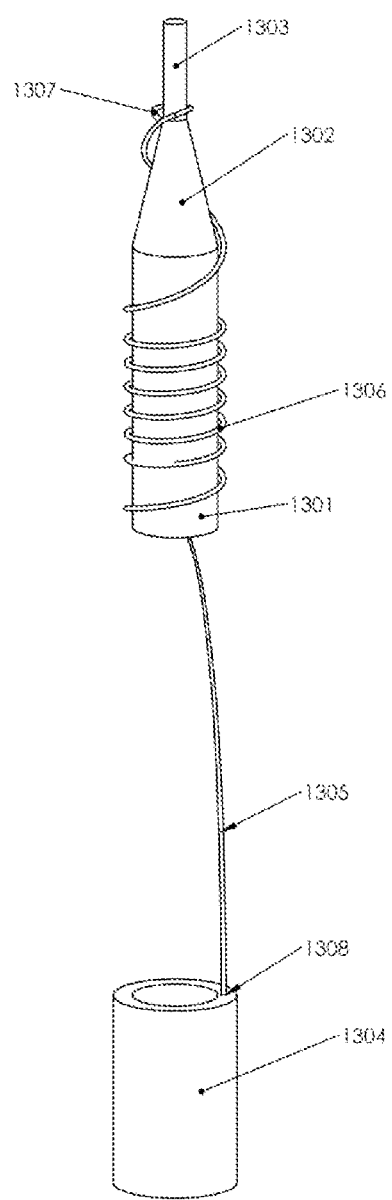

FIG. 13 shows how a palatable sleeve or other device may be tethered to the imaging capsule.

Figure 14:
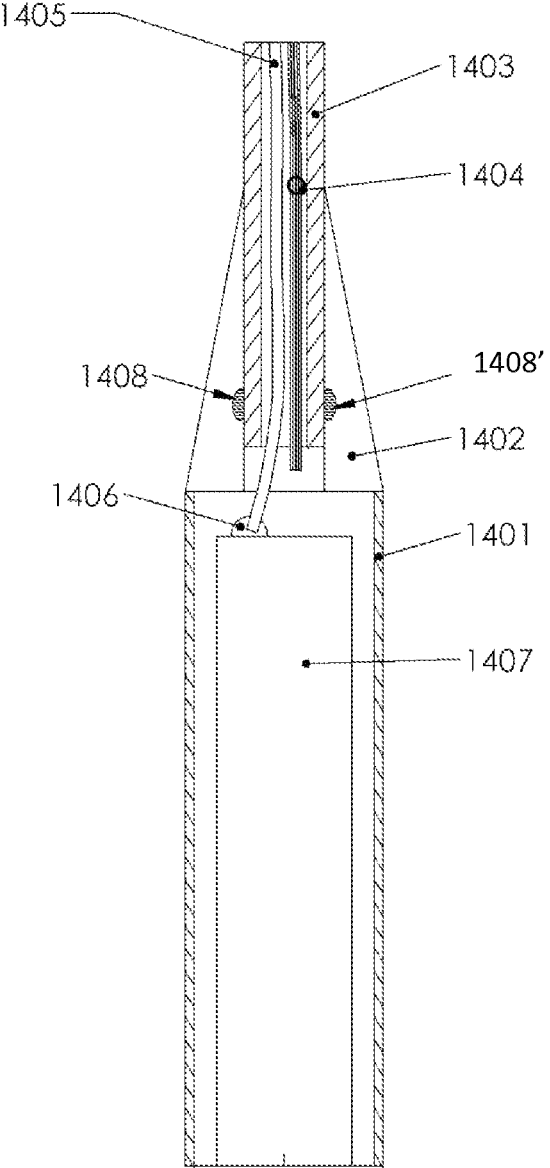

FIG. 14 illustrates how a tether may include a strand of Kevlar that is anchored internally to the imaging capsule.

FIG. 14 depicts a "critical linkage" in the form of a short segment of low tensile strength line that is connected to a higher tensile strength line that may run throughout the length of the tether.

Figure 15A:
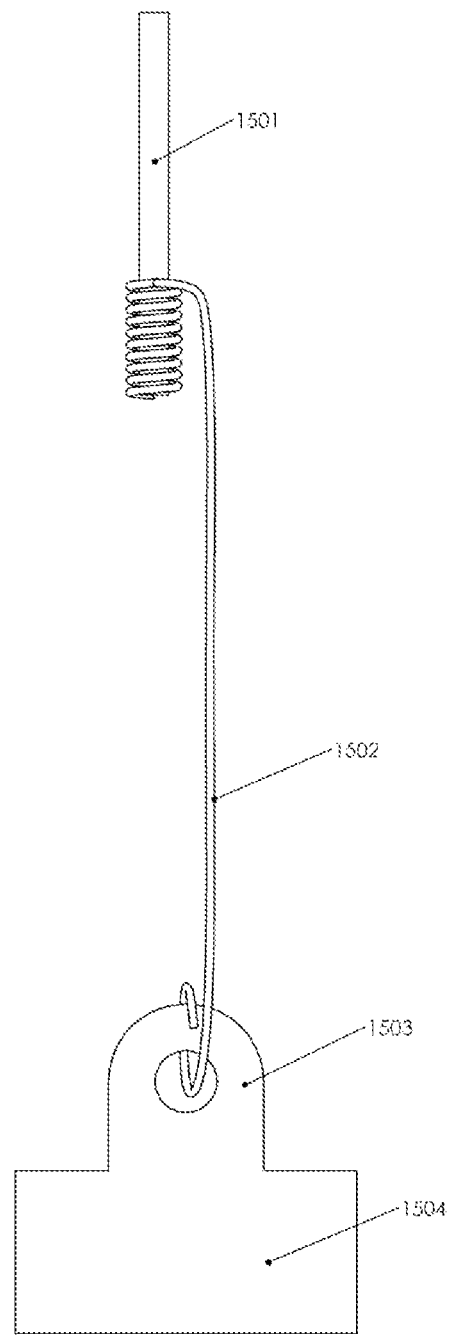

FIG. 15A is a diagram illustrating a mechanism for releasing the imaging capsule.

Figure 15B:
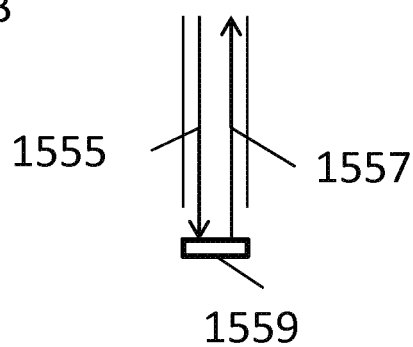

FIG. 15B is a diagram illustrating a continuity loop for sensing release of the imaging capsule.

Figure 16:
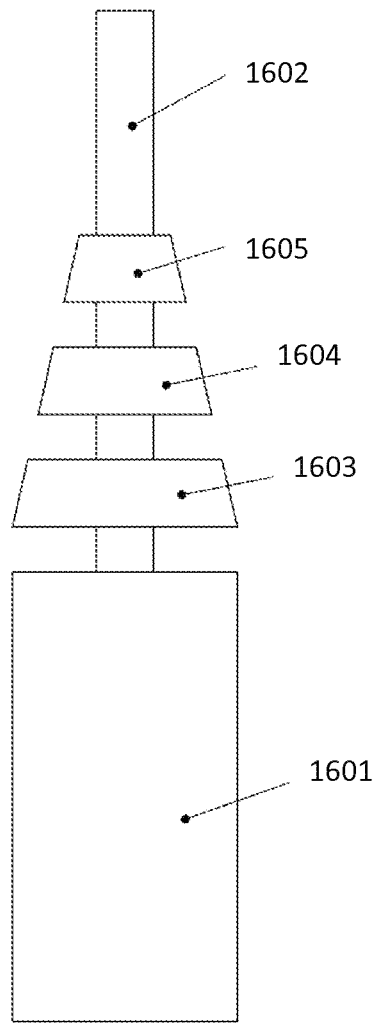

FIG. 16 shows how the tapering portion of an imaging capsule may consist of separate beaded segments threaded onto the device tether, and may be allowed to slide on the tether. The beads may be made of high density material such as tungsten.

Figure 17:
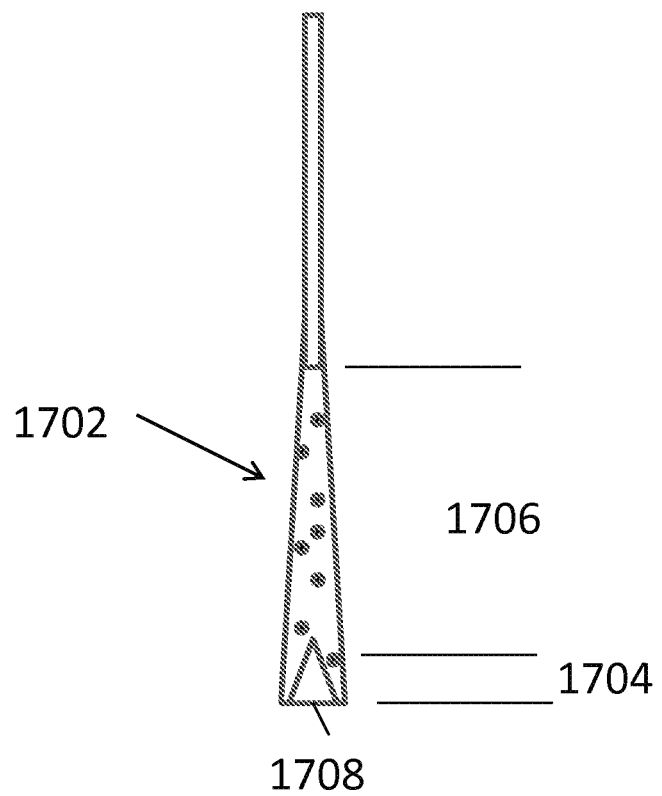

FIG. 17 is a diagram showing additional features of an esophageal probe.

DETAILED DESCRIPTION

Summary

Described herein are enhancements to an endoscope; more generally, any device in a lumen may benefit from its advantages. A typical application of the endoscope is tethered endoscopy, a term used herein to describe the use of an imaging device that is attached to a flexible linkage such as a cable that can provide only pulling forces on a terminating payload that includes a device for imaging (imaging capsule, or "capsule").

The improvements described therefore relate primarily to an endoscope comprising a flexible tether terminated by an imaging capsule.

For purposes of description, it is useful to consider three stages of an examination using a tethered endoscope:
1) Introduction, which includes swallowing and descent through the esophagus;
2) Imaging;
3) Device retrieval.

While imaging typically overlaps with the other two activities, it is useful to keep the three conceptually separate in the material that follows. Each of these stages requires different and often incompatible optimizations in the properties of the device. Reconciling these incompatibilities yields a fully optimal design for all stages of the examination.

A "palatable sleeve," palatant, or swallowing aid fits around the imaging capsule providing the necessary ingestible mouthfeel. Palatants possess sensory properties typically falling under the categories of tactile, taste, as well as smell that allow a device such as a tethered endoscope to be more easily tolerated. The swallowing aid may consist of a digestible substance such as a hydrocolloid, and it may have added flavor. It may also consist of non-digestible material (e.g., low-durometer silicone elastomer material) that mimics palatability. The augmentation of the imaging capsule diameter provided by the swallowing aid also allows for peristaltic action to be more effective in propelling the device downward through the lumen. The swallowing aid can also serve as a vehicle for containing added weight that can assist in decent of the device through the lumen as detailed below.

Peristalsis, Friction, Gravity & Pull

Peristalsis and gravity are the two main forces enabling progression of the imaging capsule through the lumen. A larger diameter device facilitates greater peristaltic "grip." Peristalsis entails a constriction of the esophageal lumen. If a band of smooth muscle contracts just proximal to the capsule and its palatable sleeve, substantial force may be transmitted by actively pulling on the device. On the other hand, if the operator simply holds the tether and capsule in place, the constricting peristaltic ring of smooth muscle may build up less force, and the constricting wave might then be more likely to pass over the device without detaching the sleeve. If the operator holds the tether loosely, the peristaltic constriction can then push the palatable sleeve and propel the imaging capsule downward.

Two forces therefore may be in play: smooth muscle contraction (peristalsis) that can exert downward force on the imaging capsule and sleeve, and a pulling motion on the tether that exerts upward force. To understand the properties of the device and how it may be used, it is useful to consider which of these forces is active and which of these forces is retentive.

When the operator is holding the tether in place and a peristaltic contraction comes in contact with the capsule, force builds up in proportion to what can be actively created by the musculature. In this instance the tether force is retentive. Being limited by the amount of active force that a contraction can create, by holding the tether in place, the peristaltic wave may be made to ride over the device without detaching the swallowing aid, i.e., the palatable sleeve. Alternatively, a contraction of smooth muscle may be encountered while pulling the capsule upward. In this case, very large forces can build up by pulling on the tether, as the contracted muscle, acting in a retentive mode, acts as a firm mechanical barrier. In this instance, a quick tug of the tether may easily dislodge the sleeve. This tug may require little displacement of the operator's hand, especially if there is limited compliance within the tether. The tether compliance can be reduced substantially by including a non-compliant member, such as Kevlar thread, along the length of the tether.

Experiments with tethered imaging devices demonstrate that gravity is a very useful force in enabling the device to progress through the lumen of the esophagus. During the exam, the esophagus ideally will be aligned vertically, such as when the subject sits or stands. Whereas muscular peristalsis is a less reliable agent for exerting positional control on a device, a gravity controlled device can be allowed to drop into a very precise position.

Peristalsis may work to pull away the sleeve while the device is still in descent mode. Experiments have demonstrated that operator technique, together with a certain degree of sleeve mechanical resilience and lock tightness, can serve to maintain the sleeve's position on the capsule during passage of a peristaltic wave. The presence of the sleeve enables constricting musculature to more easily propel the endoscope down the lumen.

Low Friction

Low friction surfaces at the taper and capsule can be useful for retrieval of the device; moreover, having a low friction surface throughout much of the length of the tethering cable is also useful, especially in allowing gravity to work on pulling the device downward into the esophagus during introduction. Assuming the cable is very flexible, as desired, cable friction operating against tissues results in appreciable resistance to the downward pull of gravity of the device. Lowering the surface friction of the cable is therefore highly advantageous.

The weight of the capsule and any related terminal structures must work against other forces—primary friction—that restrict the descent of the device when the lumen is open. Friction occurs wherever the linkage is in contact with another non-moving structure, such as tissue within the mouth, pharynx or esophagus. When downward forces exceed frictional forces, the device can travel downward, enabling it to gather images of more distal regions of the esophagus such as the esophagogastric junction. It is useful therefore to allow for portions of the device—including the tether, capsule and sleeve—to have low friction surfaces.

Low friction surfaces may be accomplished by the use of lubricous or hydrophilic coatings. Alternatively, low friction materials such as certain medical catheter-grade silicones may be used.

Significant aspects of the present tethered endoscope include:
1) An imaging capsule attached to the distal end of a flexible cable serving as a tether, the capsule having a light source and a proximal taper to facilitate withdrawal of the device.
2) Lubricious or low friction surfaces along the tissue-contacting portions of the device.
3) Means to guide illumination light from inside the imaging capsule to the field of view.
4) A palatable sleeve to be placed around the capsule whose sensory properties, which may include mouth feel and taste, mimic that of easy-to-swallow food.
5) Means to enable the palatable sleeve to detach from the capsule as controlled by a degree of pulling force on the tether.
6) Means to facilitate alignment of the imaging capsule within the esophageal lumen.
7) Means to tether a palatable sleeve to the imaging device.
8) Means to incorporate a cell collection device such as a sponge.
9) Means to reduce longitudinal compliance of the tether with a member such as Kevlar thread.
10) Means to enable the imaging capsule to detach as controlled by a degree of pulling force on the tether.
11) Dense material added to the distal region of the device primarily to serve as ballast weight, facilitating travel down the lumen.

The foregoing aspects may of course be present in various combinations, with or without other complementary features.

Aspects of the present esophageal probe, in its several embodiments, include the following.

An esophageal probe includes a tethered imaging capsule, and at least one swallowing aid configured to be temporarily attached to the tethered imaging capsule and, when detached, to be digested or passed through a user's bowel.

The swallowing aid may include an elastic lock mechanism that couples it to the tethered imaging capsule. The esophageal probe may be configured such that the swallowing aid detaches from the imaging capsule by operation of a primary tether coupled to the imaging capsule. The swallowing aid may be tethered to the imaging capsule by at least one secondary tether. The primary tether may include a component having low longitudinal compliance. The esophageal probe may be configured such that operation of a primary tether coupled to the imaging capsule detaches the imaging capsule from the primary tether.

Palatability may be enhanced in various ways. For example, the swallowing aid may be flavored; it may be colored to enhance palatability; it may be scented to enhance palatability; it may be provided with a tactile property to enhance palatability, or textured to enhance palatability. The swallowing aid may include agar, silicone, gelatin, etc. In the case of gelatin or like material, the swallowing aid may be configured to dissolve or melt during or after swallowing.

The esophageal probe may include a cell-collection feature coupled to the imaging capsule or tether, such as a sponge material.

Descent of the esophageal probe may be promoted in various ways. For example, the esophageal probe may include at least one weight-increasing feature such as high-density metallic material. In one embodiment, the high-density metallic material has a density that is at least 30% of the density of tungsten. The primary tether may be coupled to the imaging capsule so as to form a taper that tapers along the primary tether in a direction away from the imaging capsule. A weight-increasing feature may include a plurality of beads within a region of the taper. The weight-increasing feature may include metallic particles doped or distributed within a region of the taper. The taper may include a proximal body region and a distal tail region, wherein the proximal body region includes a solid metallic body and the distal tail region is flexible and is at least twice as long as the proximal body region.

The swallowing aid may include one or more alignment features, such as fins, configured to align an axis of the imaging capsule with an axis of a patient's esophagus.

The imaging capsule may include means for providing forward illumination. Forward illumination may be provided by a light source and a plurality of optical fibers coupled to the light source, wherein optical fibers of relatively smaller diameter are configured to form an illumination ring. In accordance with another aspect, forward illumination may be provided by a light source and a plurality of light guides coupled to the light source, wherein the light guides have a larger diameter.

A method is described for administering an esophageal exam to a patient, including attaching a swallowing aid to a tethered imaging capsule to form an esophageal probe, and the patient swallowing the esophageal probe.

The method may further include causing removal of the removable swallowing aid, and withdrawing the tethered imaging capsule from the patient's esophagus. Causing removal of the removable swallowing aid may include an operator operating the tether of the imaging capsule. During swallowing, at least part of the esophageal probe may be coated with a lubricious or other low friction coating.

In accordance with other aspects, an esophageal probe includes a tethered reusable portion and a one-time-use portion, wherein the tethered reusable portion is configured to be retrieved from a patient's esophagus and the one-time-use portion is configured to be swallowed by the patient.

In accordance with other aspects, an esophageal probe system includes a tethered imaging capsule removeably coupled to the tether, the tether including at least one linking member critical for maintaining connection of the tether, its wires, and other contents to the imaging capsule, the linking member configured to be broken or disconnected in response to operation of the tether such that the imaging capsule might become free from the tether.

The esophageal probe system may further include at least one swallowing aid configured to be removably attached to the tethered imaging capsule and to be digested or passed through a user's bowel.

Circuitry may be provided for sensing severing of the at least one conductor and for deactivating the imaging capsule.

DESCRIPTION

Figure 1A:
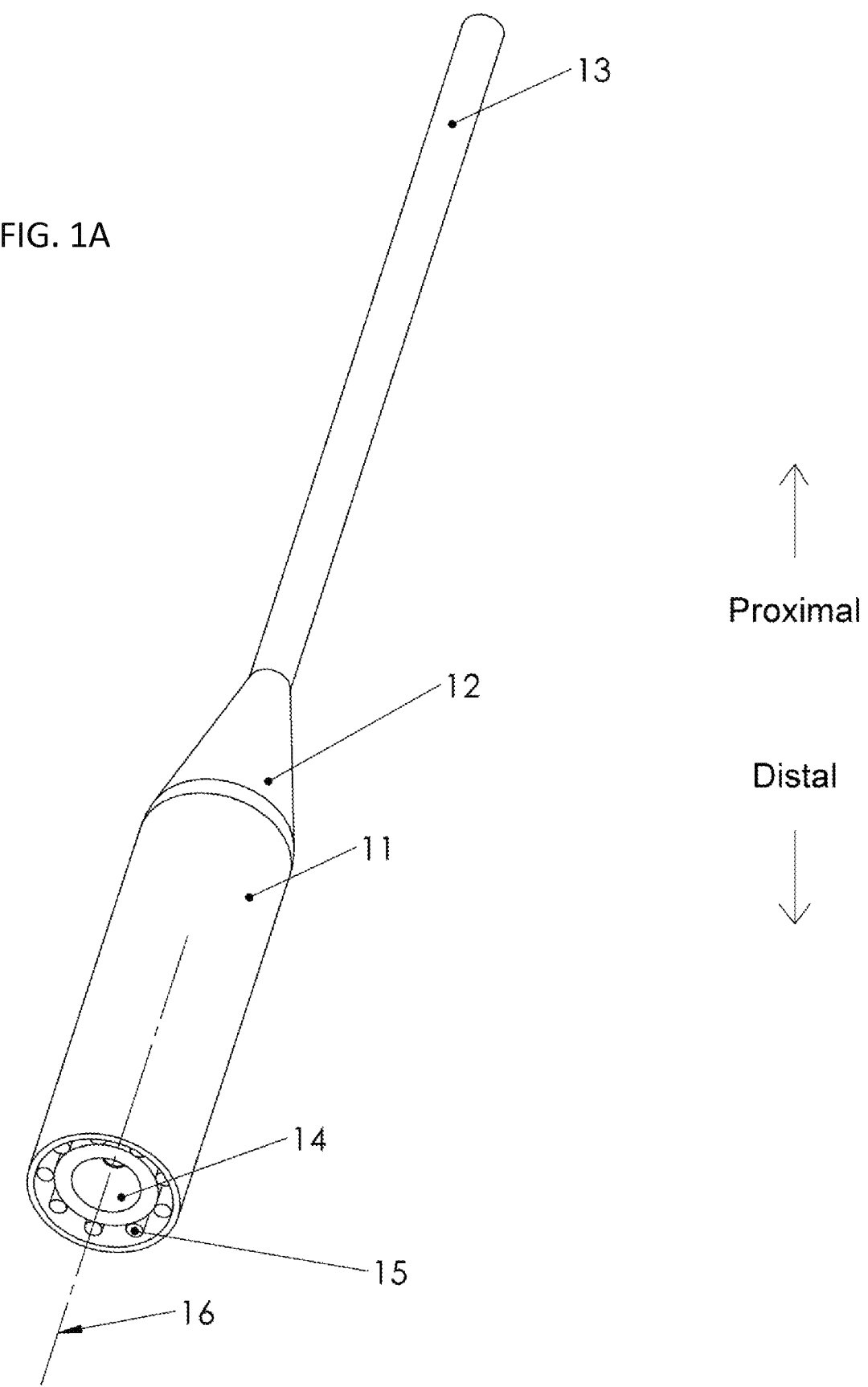
FIG. 1A depicts the general design of the distal end of a tethered endoscope that includes an imaging capsule.

An exemplary embodiment of a tethered endoscope has the structure shown in FIG. 1 wherein an imaging capsule 11 merges into a flexible tether 13 by way of an intermediate member 12 in the form of a taper. The drawing illustrates the proximal and distal directions. When imaging the esophagus, proximal is toward the mouth and operator and distal is toward the stomach. The imager has a front aperture 14, and integrated in the front is a ring of illumination 15 formed by fibers. The outmost optical element 14 of the imaging optics may be a coverslip formed by a thin optically clear plate. The device has a cylindrical central axis of symmetry 16. The imaging capsule is typically in the form of a video camera, but it may consist of other imaging technologies such optical coherence technology (OCT).

Figure 1B:
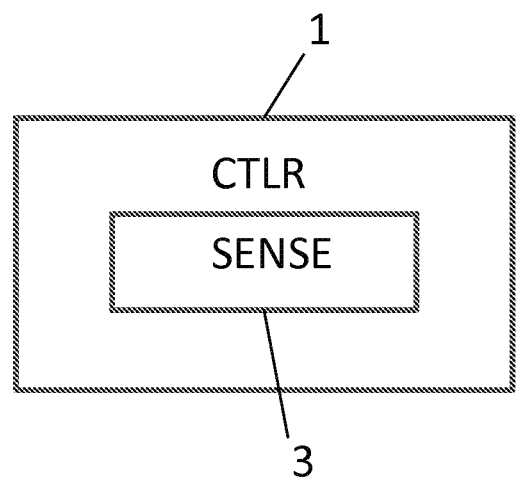
FIG. 1B is a block diagram of a controller box for controlling the tethered endoscope of FIG. 1.

The tether 13 generally is constructed as a portion of flexibly jacketed cable, being long enough to enable the imaging capsule 11 to reach the furthest reaches of anatomy. Because the cost per unit length of the tether may be high, and because signal quality may degrade if it is too long, the device may be designed to limit the overall length of the tether to that which is minimally required—e.g., the typical distance from the mouth to the stomach. The tether 13 may therefore be connected proximally to a section of more general purpose cabling that terminates at its proximal end in a connector to be plugged into a controller "controller box" receptacle, an example of which is shown in FIG. 1B. The controller 1 provides electrical power, timing, control signals and other electronics for video signal acquisition. Circuitry 3 is provided for sensing if and when a link to the imaging capsule is disconnected, as described hereinafter, so as to deactivate the electronics and de-energize signal wires.

The tether 13 should be sufficiently flexible so as to require minimal energy to induce the deformations necessary while being drawn through the mouth, pharynx and other structures. Downward forces such as gravity or peristalsis must overcome both friction and any tendencies for the cable to hold its form. A highly flexible polymer cable jacket is therefore warranted, as provided by materials such as silicone rubber or polyurethane. A desirable tether cable diameter may be 1 mm or less so as to minimize discomfort and to reduce the likelihood of a gag reflex.

Internally, the capsule comprises a camera typically composed of an electronic (e.g. CMOS or CCD) imaging sensor, a lens assembly, and a thin coverslip of optically clear plastic. An air-gap can exist between the coverslip and the outermost lens element, yielding an ability to image underwater.

Illumination can be provided by LED's mounted beyond the periphery of the lens, or via one or more LED's that are contained within the imaging capsule, but whose light is piped outward via optical light guides. Light guides provide an alternative to placing light sources at the surface of the device, where mounting, interconnecting and dissipating heat can be challenging.

Light guides may be used in various ways. One variant shown in FIG. 2A uses a bundle of optical fibers to capture light from each of one or more LEDs, and to then route the light amongst the fibers to target areas such as the periphery of the external capsule, where they can provide illumination of the field of view. Thus, multiple fiber end points may encircle the perimeter of the face of the capsule. Optionally, diffusers may be added overlying the end points, taking the form of diffraction gratings or other standard means.

Extending from the proximal portion of the imaging capsules may be a taper consisting of silicone or other soft polymer, although high-durometer implementations are also possible. This taper avoids sharp discontinuities but may also be of considerable utility in enabling retrieval of the device. The esophagus possesses smooth musculature capable of very tight constrictions. A constricted esophagus may make it very difficult to retrieve the device. The addition of a taper provides a mechanical wedge effect to pry open the lumen enough to enable device retrieval. Providing the taper with a low friction surface can also be of great value in retrieval. Options include lubricious coatings or a direct low-friction structural formulation of the flexible taper. Certain silicones exhibit both a very low durometer and very smooth surfaces when in contact with water. These materials may be structural or applied as surface coatings.

Proximally, the camera body merges with the tether via the taper, allowing easier pullout in the presence of peristalsis. While much of the body of the device may be rigid, the taper may be flexible or comprise moveable segments so that the capsule and taper do not present excessive rigidity that would impede swallowing or removal of the device.

The specific mechanical properties of the taper may be designed to aid in insertion, imaging and/or removal. To accentuate the wedge effect, the taper can be lengthened, and may be as long as or longer than the imaging capsule. A long taper at times needs to be able to bend and deflect laterally—otherwise it may be difficult to swallow. When encountering a constriction during a muscle contraction, squeezing of the taper material longitudinally may result in a bulge that is easily obstructed by the constriction, thus negating the intended goal of easing passage of the device through the constriction.

One class of embodiments avoids this problem by ensuring that the tether is minimally susceptible to radial (or volume) compression and resists longitudinal shearing strain. As an example, a spongiform tether can undergo volume compression, which makes it undesirable. On the other hand, there are many polymers including PTFE, polyethylene and others that can achieve ease in lateral deflection while preserving their mechanical stiffness when a constriction is encountered.

Embodiments described herein that include using one or more tapering beads can provide a similar set of properties. The taper comprises separate segments or beads, and may be covered with a flexible polymer shell to eliminate external discontinuities that tend to be accentuated when the beads are deflected. Consisting of metal or other stiff materials, the beads prevent compression and longitudinal shearing.

In another embodiment, the taper material is designed to be compressed and to partially extrude through a constriction. In this case, the taper may be anchored proximally to the tether or a flexible tube that wraps around the tether. When the taper encounters a constriction, the distal non-anchored portion can be pulled, thinning out the body of the taper but also distending it so that its distal portion slips over and covers a portion of the imaging capsule. Upon completion of passage through the constriction, shape memory may enable the taper to recover its original form.

Figure 2A:
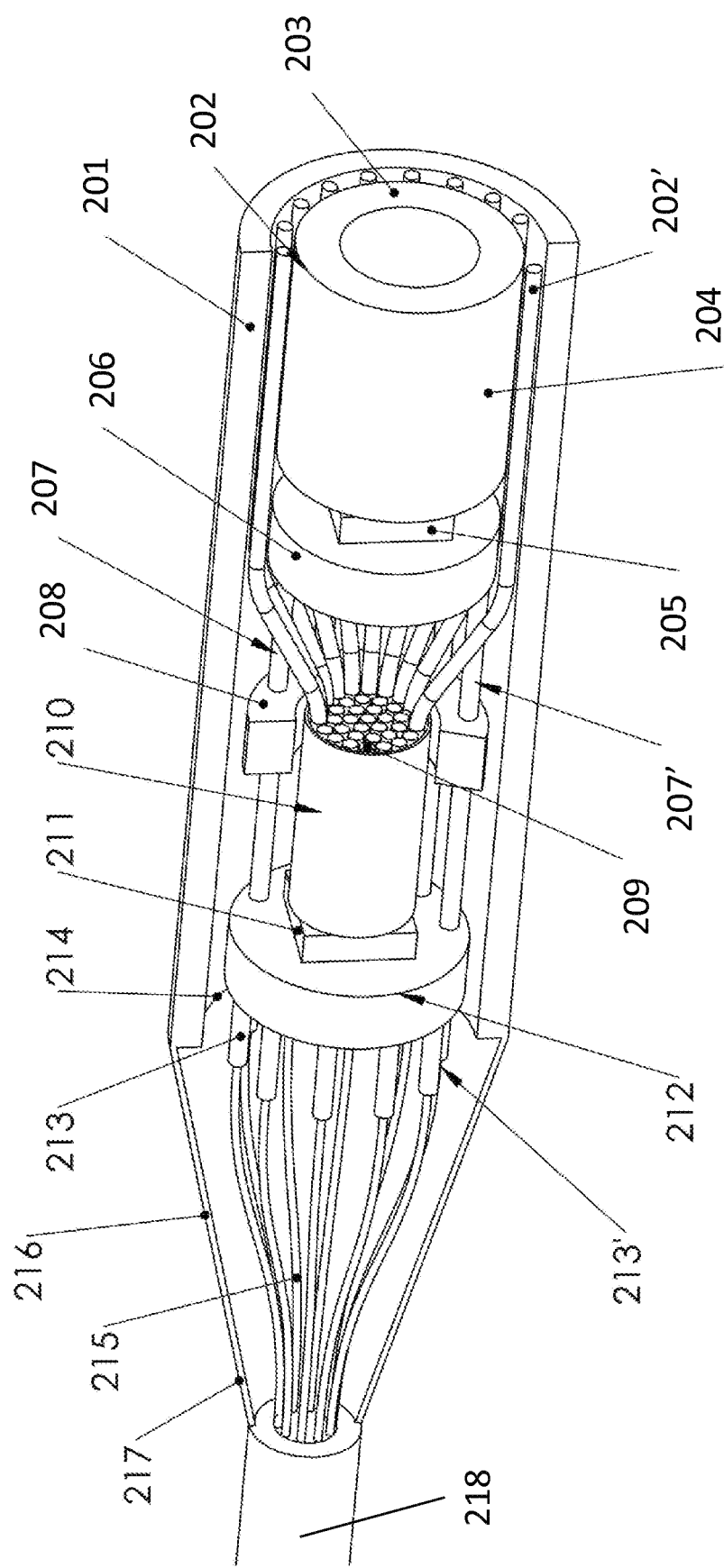
FIG. 2A illustrates the use of multiple small diameter optical fibers for routing light from a light source to the field of view.

Construction of the imaging capsule in FIG. 2A includes an outer cylindrical shell 201 that serves as mechanical and water barrier. The device is operated by means of a cable or tether 218 out of which emerge electrical leads 215 that connect with a light source 211, which might typically be one or more LED's, and an electronic camera sensor 205, typically being a CMOS or CCD sensor. Each wire is soldered to a stiff lead 213, 213', each of which enters respective vias arranged within a first printed circuit board assembly (first PCBA) 212 that houses the LED 211. The distal surface of the LED contains the emitter. Some of the stiff leads may be soldered to the vias of the first PCBA enabling power and control for the LED. After emerging from the first PCBA, the stiff leads pass through vias of a collector ring 208 and emerge as leads 207, 207' and are soldered into vias or onto pads of a PCBA 206 that houses the sensor 205. A lens assembly 204 provides focusing of the image onto the optically sensitive portion of the sensor.

Proximal to the emitter of the light source 211 is a bundle of optical fibers 210. One embodiment uses optical fibers of relatively small diameter, for example 250 micron multi-mode plastic optical fibers with fluorocarbon polymer sheaths. Each fiber independently transmits light with minimal loss. The fiber bundle is fitted within the central hole of the collector ring 208. The proximal ends of the fibers receive light from the LED. To enhance coupling of light from the LED, the space between the emitter surface and the fiber bundle can be potted with clear polymer such as optical-grade epoxy. Upon emerging from the collector ring, the fibers continue along the periphery of the image sensor PCBA and lens assembly, and terminate as cut ends 202, 202' in a plane coincident with the aperture surface 203. The aperture surface may include the final surface of the lens assembly, or it may consist of a coverslip. The design of FIG. 2A includes a taper 216 that joins tether 218 at a junction 217.

Figure 2B:
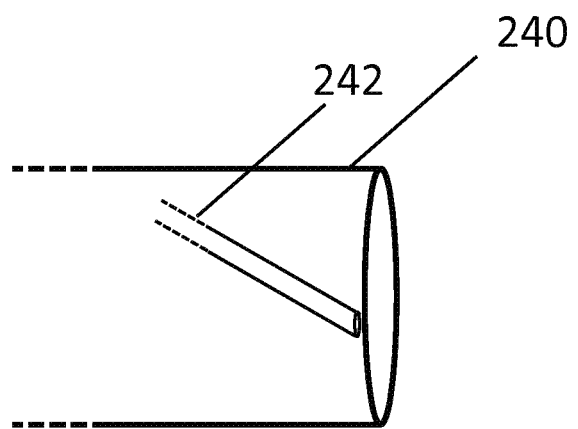
FIG. 2B is a diagram illustrating an arrangement for producing a desired light distribution.

To spread the light exiting from light fibers 202, 202' over a very wide field of view, diffuser elements may be placed over the fiber terminations. Moreover, the fibers may be so that at their terminus they are skew rather than aligned with the central axis of the device; e.g., they may be twisted in a helical pattern within the imaging capsule so that they wind around the lens assembly 204 in a spiral pattern. Spiraling the fibers does not add to the diameter of the assembly, but it does allow the light to concentrate less in the vicinity the central axis. The fibers come out skewed instead of pointing straight, such that the light from each fiber is deflected away from the center axis. Also, if the fibers are cut parallel to the front plane, then refraction deflects the light further away as well. The light from an individual fiber may be analogized to a laser beam (although in actuality it is more of a diffuse spot). Normally, the beams from the straight fibers project onto a circle. In a spiral arrangement, the beams deflect to a point on the tangent to the circle, resulting in their being further away from the center axis. When beams from the fibers are added up, the net effect is a broader spot pattern due to the spiral. This type of spiral arrangement is illustrated in FIG. 2B, showing an imaging capsule 240 and a representative fiber 242.

Referring again to FIG. 2A, note that the fibers start proximally on the center axis and then cross the electrical leads, which are on the periphery. In addition, the use of the ring 208, which passes the optical fibers through its center hole and the electrical leads through vias, allows for the use of a single large LED and yields a relatively even distribution of light.

Figure 3:
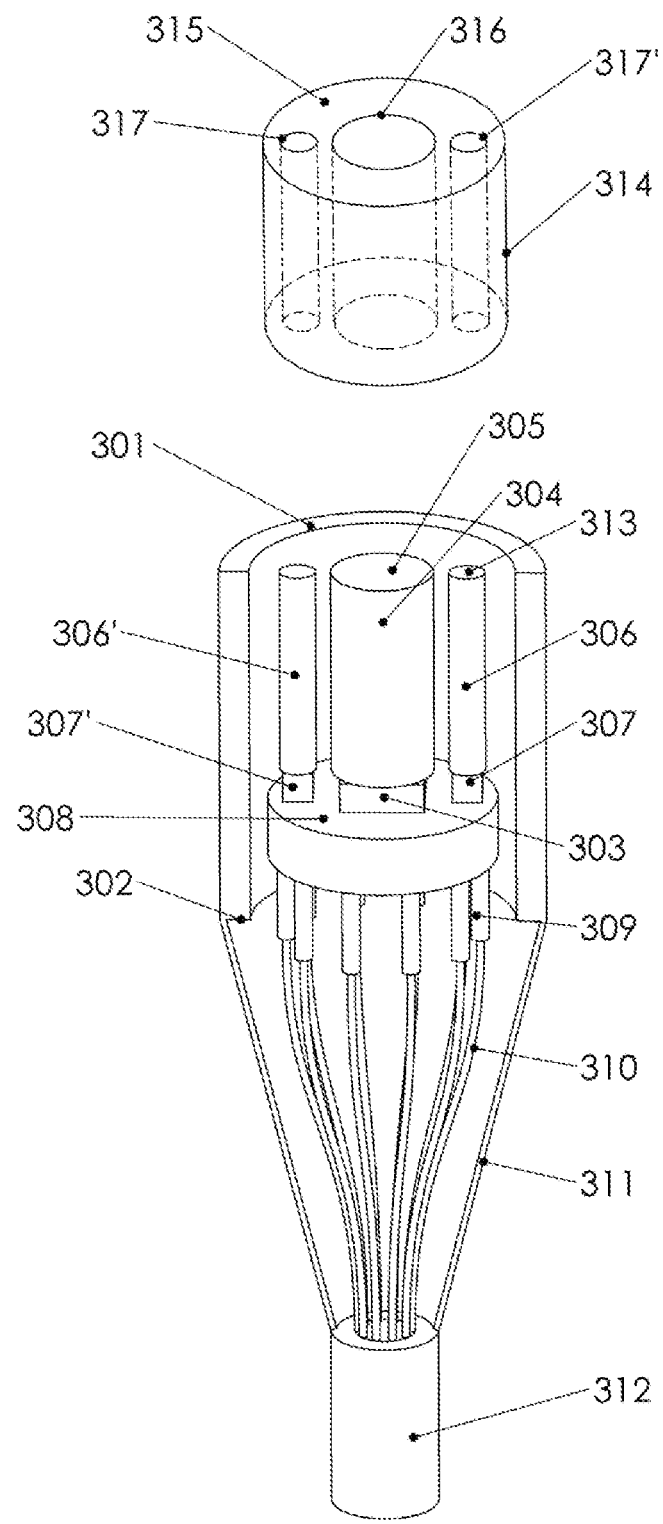
FIG. 3 illustrates the use of light pipes for routing light from a light source to the field of view.

Another embodiment shown in FIG. 3 involves using two large diameter light guides to pull light from the LED to the periphery, again using diffusers as needed to spread the light across the field of view. Bundles of smaller fibers may also be used. In both FIG. 2A and FIG. 3, advantages include being able to place the one or more LED on the same board as the sensor, and to keep LED heat away from tissue. The tubular shell 301 houses an image sensor 303 in association with an imaging focusing lens assembly 304 with face 305. Two light guides 306 and 306', in this case segments of plastic optical fibers with cladding, are affixed to the emitter elements of LEDs 307, 307'. Optically clear potting can be used to efficiently couple light from the emitters into the light guides. Light emerges from the light guide surface 313. The sensor sits upon PCBA 308 into which leads 309 are connected, the leads 309 extending from wires 310 that emerge from the tether jacket 312. The tubular shell 301 merges proximally at junction interface 302 with a taper 311 that extends circumferentially about the device, forming a seal. The taper merges proximally with the tether.

A detached view of a mating element 14 is shown that includes mating holes 317, 317' for the light guides 306, 306' and a hole 316 that matches the lens assembly 304. The mating element slips over the mating structures, the proximal surface of the mating element coming in contact or close proximity with the distal surface of the PCBA 308.

During introduction of the device into the subject, it is advantageous to have the device appear and behave as being palatable, so that the patient has minimal reservations about swallowing it. It should have a form, size and consistency that facilitate the act of swallowing and descent through the esophagus. For example, an imaging capsule enclosed in a roughly 4 mm or smaller diameter stainless steel cylindrical tube of 1-2 cm length attached to a 0.7 mm to 1.0 mm flexible cable can present considerable psychological barriers to ingestion. Furthermore, even if one may succeed in initiating actions to swallow the device, voluntarily passing it through the pharynx into and down the esophagus may be very difficult due to the small size and weight of the imaging capsule and the presence of the tether.

One approach allows parts of the device that come in contact with the oral cavity and pharynx to be imparted with a surface coating of palatable material.

The applied palatable material may consist of most any edible substance that can be applied to the surface so as to adhere long enough to allow for the required sense of palatability. Saliva, water, gravity or other influences may quickly disperse the material, but as long as it adheres to the device surface long enough for it to pass beyond the oral cavity and pharynx, it can provide the advantages from imparting a sense of palatability. There are many approaches to applying palatable material, which may be performed on the packaged device or during the examination.

Figure 4:
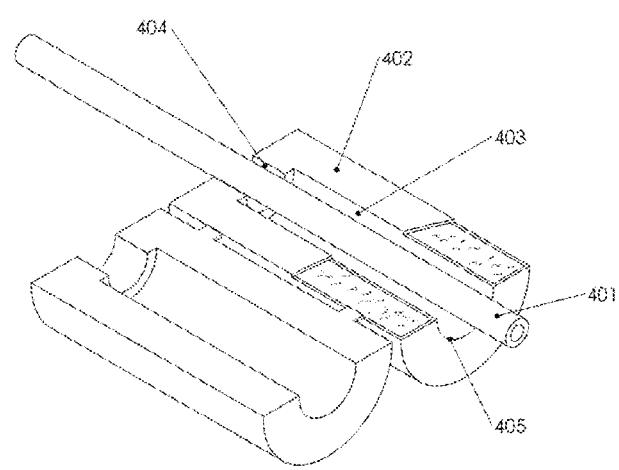
FIG. 4 is a diagram of an applicator that may be used to coat the imaging capsule and its tether with a palatable coating during the examination while the imaging capsule descends down the esophagus.

In one embodiment, shown in FIG. 4, a tubular device comprising an applicator body 402, which may be formed as two halves connected with a hinge, may be filled with palatant such as thick syrup. The device may then be clamped onto the tether 401. As the tether 401 passes through the device, which can be held in place by the exam subject, operator or other means, it obtains a coating of palatant. In the illustrated embodiment, the palatant is a liquid palatant placed in a cavity 403. A proximal opening 404 is designed to allow tether to slip, but no fluid will emerge if the tether is pulled in the proximal direction relative to applicator. A distal opening 405 provides clearance and allows palatant to slip out and coat the tether as it moves in the distal direction relative to applicator.

A palatant may also be assembled into the device, especially if it is made from chemically inert material such as silicone rubber. Alternatively, the palatant may take the form of a coating upon certain surfaces such as the side of the capsule or the tether. For example, it might be formed as a sleeve by dipping the device into a liquid that can then harden about the device, or if left as a thick liquid, it may adhere long enough to be effective during introduction of the device. The sleeve may then comprise one or more layers of gelatin or edible confection that can wash away or melt away quickly when swallowed. When applied as a coating or dip, if the palatant is not intended to be washed away quickly during or after swallowing, it may be necessary to ensure that the optical surfaces remain uncoated.

The palatant can be added just before introduction of the device into the mouth. It can be packaged separately similar to an item of food or candy.

Experiments have shown that there is an optimal range of holding strength for any locking mechanism, below which the sleeve slips off too easily during routine swallowing and travel down the esophagus, and above which it may be difficult for the sleeve to detach when attempting to retrieve the imaging capsule at the end of the examination. Typically the palatant, when formed of agar or other edible gel, will break apart in the presence of significant retaining forces due to constriction of the organ musculature. However, during introduction of the device and its descent into the lower esophagus, the palatant provides some extra weight, aiding descent, and possibly some needed traction for peristalsis to aid in advancing the device through the lumen.

One exemplary embodiment involves using a color-tinted, lightly-flavored, rubbery hydrocolloid as a sleeve to wrap around the imaging capsule without interfering with the optical imaging performance. The choice of material composition—from among a variety of material compositions, including non-hydrocolloid based compositions—influences the ability to overcome the psychological and physical barriers to swallowing the imaging capsule. Gelatin provides many excellent properties in terms of mouth-feel and rigidity. However, it tends to melt just below internal body temperature, and therefore other materials may be preferred.

One useful ingredient for the palatable sleeve is agar. Sources publically available within the food industry describe how the brittleness and poor elasticity of agar can be overcome by the addition of other ingredients such as xylitol. Colorants and flavors can be added, but caution should be taken in adding flavors, as they may trigger an excessive saliva or motility response.

Consider an imaging capsule 4.5 mm in diameter by 1.5 cm in length. One suitable swallowing aid may be constructed as a cylindrical tube of elastic agar (e.g., mixture of agar and xylitol) with an inner diameter of less than 4.5 mm, and an outer diameter of 10 mm. The length may be slightly longer than 1.5 cm, with the proximal inner diameter constriction to a slightly smaller dimension for a length of a few millimeters.

Figure 5:
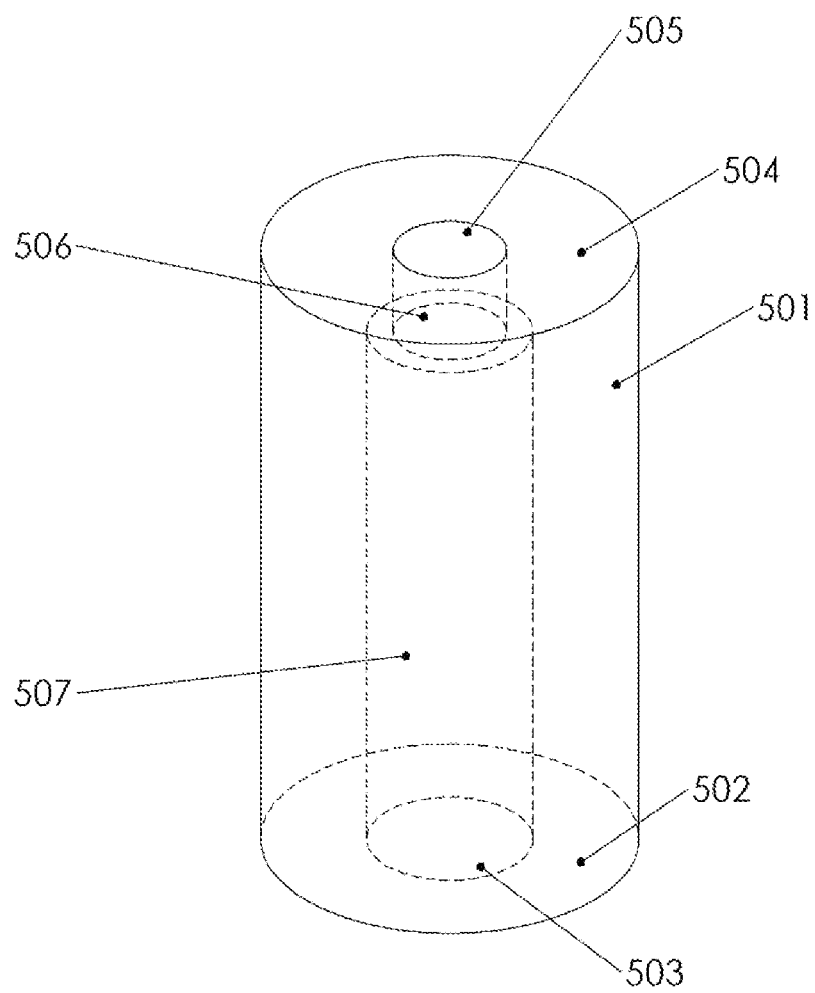
FIG. 5 illustrates a palatable sleeve that can be slipped onto the imaging capsule.

In one embodiment, a sleeve formed of palatable material provides for an enhanced sense of palatability of the device. The design of a palatable sleeve is shown in FIG. 5. The sleeve is designed as a hollow tube with wall 501 and distal front surface 502, a distal opening 503, a proximal surface 504 and a proximal opening 505. The distal opening is continuous with the main and wider portion of the hollow 507. The proximal opening is continuous with the narrowed segment of the central tube 506. This constriction can allow the cylinder to slide down the capsule, and then lock in place once the proximal portion of the tube clears the 4.5 mm diameter portion of the capsule, which as noted above, will typically consist of a proximally directed taper. Other mating forms of imaging capsule and sleeve can allow the sleeve to slide onto the capsule and be retained with some degree of locking force. In other embodiments, friction fit alone is sufficient to hold together the imaging capsule and the sleeve during swallowing.

Figure 6:
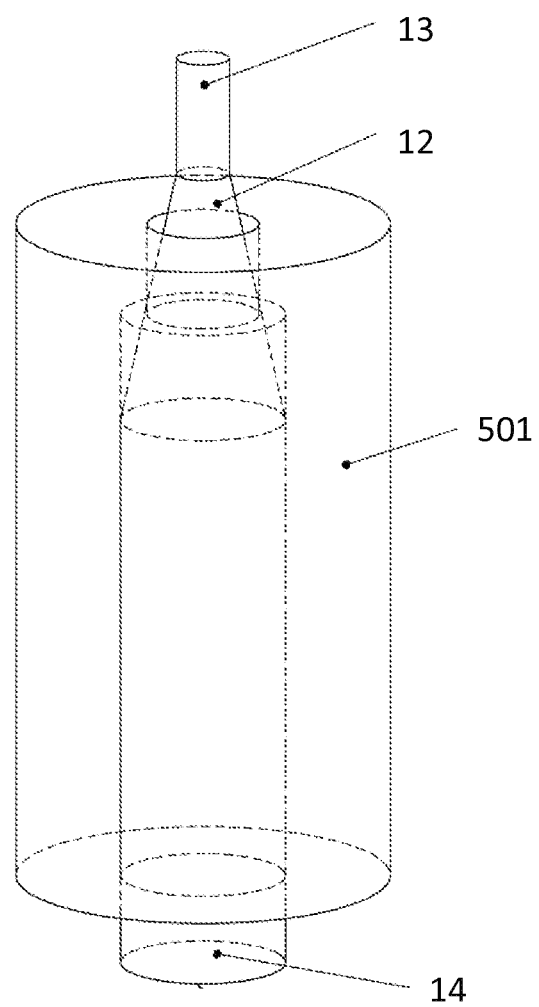
FIG. 6 illustrates the palatable sleeve attached to the imaging capsule.

FIG. 6 shows how the sleeve of FIG. 5 fits over the imaging capsule of FIG. 1, showing how the lock inhibits the sleeve from sliding distally with respect to the imaging capsule.

One embodiment allows for the sleeve as shown in FIG. 5 and FIG. 6 to be ejected from the imaging capsule when a peristaltic contraction prevents the device from being retrieved at the end of an exam. At this point, the sleeve is unnecessary if not a hindrance, and therefore a rapid tug transmitted along the tether sufficient to pull the imaging capsule out from the sleeve may be applied.

More particularly, one ejection or release approach for the palatant involves the use of high-amplitude but short-duration tension on the tether to force the imaging capsule to disengage from the sleeve. Routinely, the esophagus will undergo peristaltic contractions while the device is being withdrawn. If these contractions do not impede the device, it may be pulled out with minimal discomfort, possibly with the palatant intact. More likely, the pull from the constricted musculature will impede the device, and at this point it is desirable for the swallowing aid to be released—as achieved by a short but firm tug. This approach can work for both food-based as well as non-food based (e.g. soft silicone) palatants. For a more brittle palatant, the sharp pull forces may not cause it to cleanly slip off, but instead it might break into separate pieces or split open and therefore fall away. Thus brittleness and other properties contributing to the controlled breakup of the device may be desirable in certain embodiments.

A further embodiment entails a palatant that readily detaches once the capsule reaches the pharynx or rear of the oral palate. In this case, the idea is to provide a means to position the capsule near the level of the uvula, so that it may image upward (into the nasal pharynx) or downward, for example to observe the act of swallowing. An introducer, in the form of a flexible tube, might be used to create a comfortable feel for the patient in the back of the pharynx, helping to reduce the gag reflex. The capsule may be extending horizontally or at some other non-optimal angle if the imaging axis is along the axis of the capsule, as in the previously described embodiments. In this application, small overall diameter may not be so critical to preserve. Therefore, to create the correct imaging angle, a prism or mirror may be employed, or the design may simply enable the sensor and lens assembly to be rotated into the proper direction.

Gelatin tends to melt just below human body temperature. This property may be used to advantage to ensure that a sleeve will detach or disappear after a certain working time. Some experiments have shown that this working time may not be sufficient for normal exams and for certain sleeve designs when the sleeve comprises 100% gelatin. However, alternative materials including HPMC (hydroxypropyl methylcellulose) or mixtures might be used for at least part of the sleeve's construction, and properties of these may be tuned to ensure that the working time can meet the requirement. The gelatin may take the form of a shell, much like that of a medication capsule. Underneath this shell may be a variety of devices, such as a dry sponge that in the presence of water, expands and becomes soft but large diameter in form, enabling the device to be centered or propelled downward more easily. Taking on the added water adds weight to the distal device, promoting gravity-assisted decent. The expanded sponge may be a simple tube or have fins or other structures that assist in centering the device within the lumen.

Alternative embodiments for the palatant sleeve use a non-edible or inert material such as low-durometer silicone. The system is again designed so that the tube can slip away when smooth muscle contraction forces build up during retrieval. Weight may be added to the sleeve in the form of heavy particles, powder, or the like.

During imaging, it is important to be able to align the capsule within the lumen, so that the imaging field of view projects primarily longitudinally through the lumen. The added diameter of the sleeve allows for the imaging capsule, which typically is suspended downward towards the stomach, to be better centered within the lumen, which may be sufficient.

Another embodiment provides for flexible and collapsible structures built into the sleeve, such as fins or other projections. When the lumen is collapsed, these structures collapse around the body of the sleeve or imaging capsule. When the lumen is open, they expand and help to align the capsule within the center of the lumen.

Figure 7:
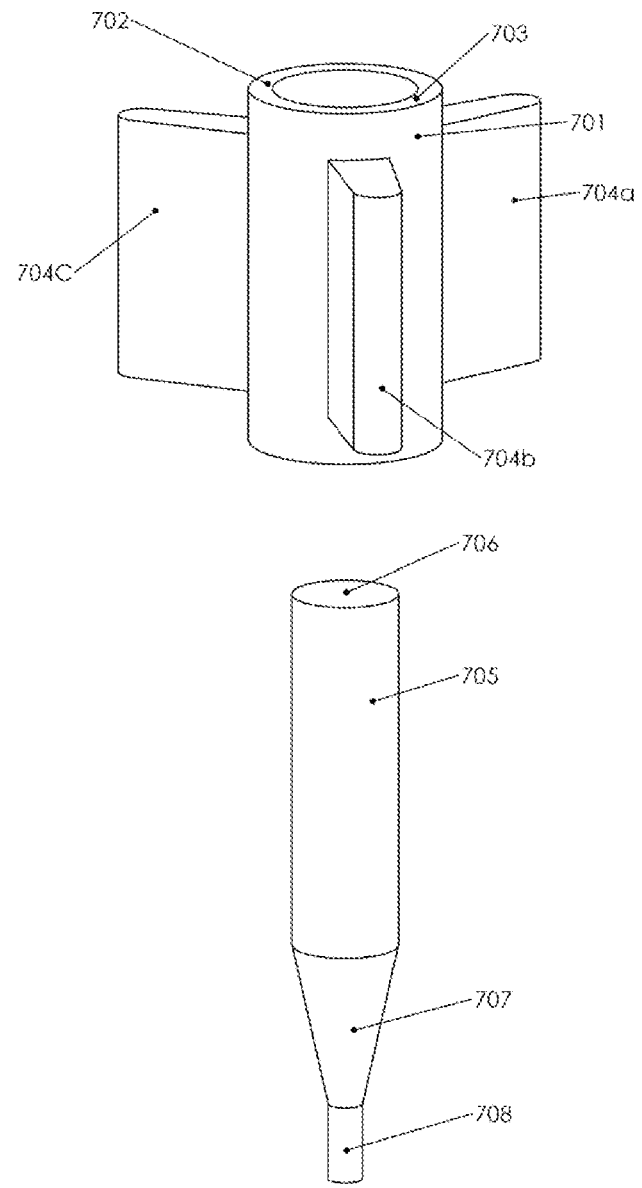
FIG. 7 shows a sleeve with fins. The sleeve is detached from an imaging capsule.
Figure 8:
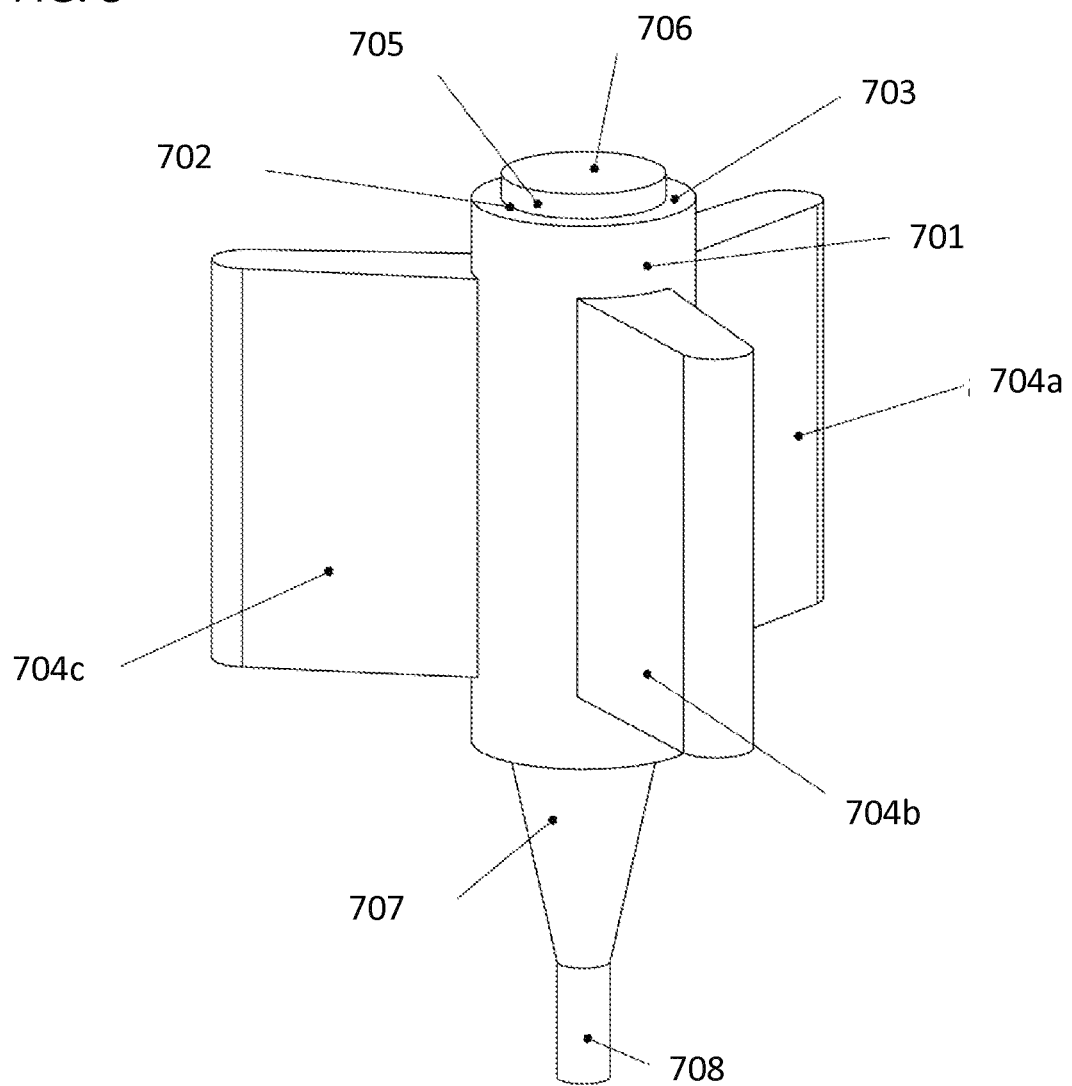
FIG. 8 shows the sleeve of FIG. 7 attached to the imaging capsule.

FIG. 1 and FIG. 8 demonstrate one embodiment in which the effective diameter of the palatant is increased by adding radiating features. FIG. 7 depicts the palatable sleeve detached from the imaging capsule. FIG. 8 illustrates the attachment of the sleeve to the imaging capsule. Referring to FIG. 7, the central body of the palatable sleeve assumes a cylindrical form 701 with central hole 702 and distal surface 703. Flexible fins 704a, 704b, and 704c emerge from the central body. The sleeve is designed to slide onto the imaging capsule 705, with its distal face 706 and taper 707 that merges with the tether 708. This design, as with others, can be formed from flexible edible material such agar-xylitol or from flexible low-durometer polymers such as various silicones.

Figure 9:
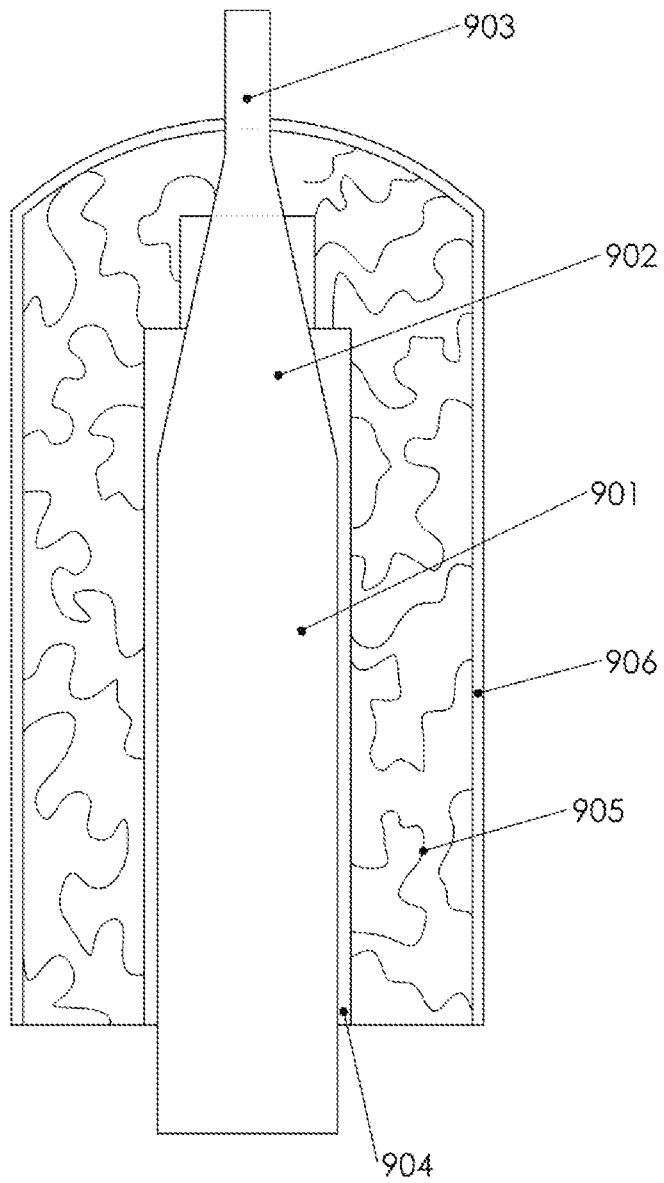
FIG. 9 shows a cutaway view of a cylindrical sponge affixed to an imaging capsule. The sponge is collapsed and encased in a gelatin capsule.
Figure 10:
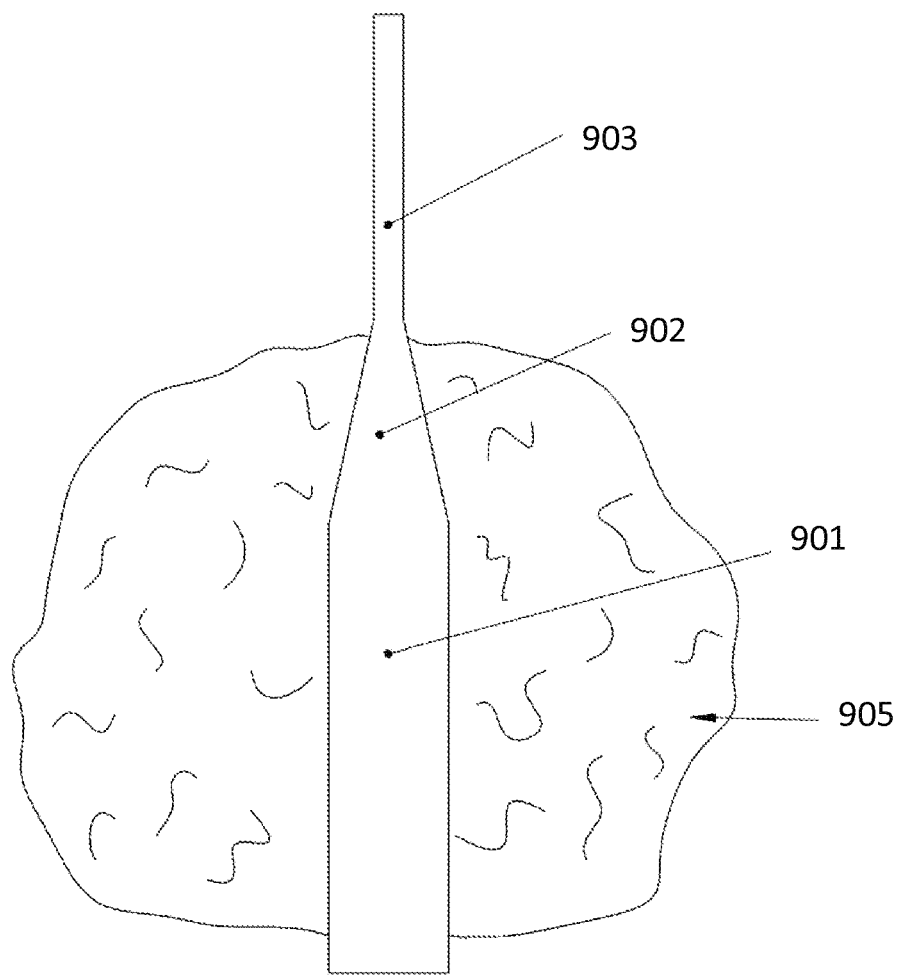
FIG. 10 shows the sponge of FIG. 9 having expanded due to contact with water. The gelatin capsule is no longer present.

Instead of hydrocolloid or similar materials, the palatant sleeve may consist primarily of sponge in a manner depicted in FIG. 9 and FIG. 10. Shown are the body 901 of the imaging capsule with taper 902 and tether 903. Surrounding the capsule is a cylinder 905 formed from sponge whose lumen 904 allows the imaging capsule to fit inside. The lumen may narrow in the vicinity of the taper to provide a locking mechanism as previously described. Surrounding the sponge is a palatable capsule 906 comprising gelatin. FIG. 9 shows the sponge compressed with the gelatin capsule intact. Exposure to water and the warmth of the body lead to an erosion of the capsule and the influx of water into the sponge. The sponge expands as in FIG. 10. This expansion can yield the advantages of previously-described in regard to alignment and other dynamics. Note that the sponge sleeve may be slid in place and be retained by forces strong enough to hold it in place during the imaging portion of the exam, but weak enough to allow the sponge to be dislodged once a peristaltic constriction is encountered while pulling the device out. Note also that the water-soaked sponge provides additional weight to the device. It may be desirable for the sponge to stay attached more permanently to the imaging capsule. This may be the case when the sponge is used to collect cytology samples, for example.

A sleeve may be created in whole or in part by wrapping a putty-like palatable material around the imaging capsule. Such an approach may start with a collection of material of one form and completely transform it into the form that is wrapped around the imaging capsule. The operator's fingers may be used to bring about the transformation, or a tool may be provided. Edible materials for this purpose may include starch or flour-based dough. Edible gums, starches, sugars, and oils may all come into play to create a limitless variety of possibilities. The palatant may be dispensed in a form that nearly matches the final form, requiring only that it be slipped over the capsule and press-fit it into shape.

Figure 11:
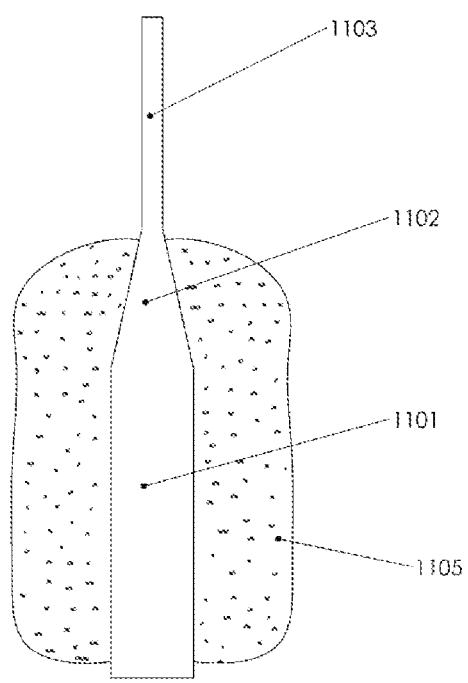
FIG. 11 illustrates the use of putty-like palatable material that the operator may manipulate into a desired form and affix to the imaging capsule.

FIG. 11 illustrates the use of such a putty-like palatable material that the operator may manipulate into desired form and affix to the imaging capsule. Shown are the body 1101 of the imaging capsule with taper 1102 and tether 1103. Surrounding the capsule is a mass 1105 formed from putty.

A sleeve may be of composite construction. An example is shown in FIG. 12, which shows imaging capsule 1201 with taper 1202 and tether 1203. Inner sleeve 1204 with lumen 1205 fits over the capsule, and may lock into place in a manner previously described. Outer sleeve 1206 with lumen 1207 may then slip over the inner sleeve, there being a narrowing of the proximal lumen or other means to lock it in place. The material compositions may differ for different ones of the sleeves and may be chosen from among many choices. As one example, the inner sleeve may be fashioned of low-durometer silicone, while the outer sleeve may be edible gel. More complex combinations involving a greater number of sleeves are possible.

The composite construction may take many forms, and it may be especially useful in certain special cases calling for a very small diameter (e.g. under 2.5 mm) imaging capsule. The inner sleeve material may provide more stable mechanical attachment to the capsule, while the outer sleeve material may provide better palatable properties or other properties helpful for propulsion. The composite design may include heavy materials such as tungsten.

There may be more than one sleeve along the length of the device, or the multiple sleeves may overlay each other and therefore be concentric. The entire device may be designed so that the layers do not separate. An example of concentric layering involving three components may include a soft pliable inner layer that includes the locking mechanism, a heavy layer comprising a metal such as tungsten, and an outer layer comprising a palatant sleeve in one of many of the embodiments described herein. Multiple strategies are possible with respect to how the sleeves detach when a constriction is encountered during pullout.

In another embodiment, the sleeve is tethered to the capsule as is shown in FIG. 13, which shows imaging capsule 1301 with taper 1302 and tether 1303. A cylindrical palatable sleeve 1304 is attached to the imaging capsule by way of tether string 1305 ("secondary tether") which forms several windings 1306 around the imaging capsule before it is affixed at the narrow section 1307. In this case, the capsule can be designed to slide off more readily, perhaps just after swallowing. FIG. 13 shows the palatable sleeve in the process of dropping away from the imaging capsule. As it drops further, the coils 1306 unwind. Earlier in the time, the coils are fully wound and the palatable sleeve fits over the coils and capsules. When attached, the relationship between palatable sleeve and imaging capsule is similar to that of FIG. 6.

When ingested, the sleeve acts as before to facilitate swallowing of the capsule, but thereafter, forces such as peristalsis or gravity pull the sleeve from the capsule. The sleeve in this case may lack the proximal constriction that serves as a locking mechanism, or the locking mechanism may fail, in which case the tether serves to preserve the utility of the sleeve despite it being dislodged from the imaging capsule. Whether the palatable sleeve is intentionally dislodged or not, peristalsis and gravity can serve to force the sleeve downward to provide the benefit of pulling along the imaging capsule.

The tether for the sleeve may be thin string that is, for example, 1-3 inches long, the thin diameter resulting in less obstruction to the field of view. The sleeve tether line may be attached to the side of the capsule via pad and adhesive, or lassoed along the proximal taper. If the sleeve and its tether are applied during exam preparation, one of or more of these mechanisms, or other convenient mechanisms, may be made available to the operator.

During pullout, it is desirable that the tethered sleeve be detachable once a substantial peristaltic constriction or other impediment to retrieval is encountered. One approach is to allow for the tethered sleeve to tear free from its tether. This may be possible if the sleeve is composed of a weaker material such as agar. Alternatively, the sleeve tether itself may be designed to break, being formed, for example, of a material with a well specified tensile strength. The sleeve tether may be threaded through a hole in the sleeve, a knot or other bulbous obstruction being used to prevent it from slipping out except when sufficiently high force is presented along the sleeve tether.

A variant on the tethered sleeve is to include an auxiliary sample collection device that may comprise a sponge or other material. When the device is extracted by the operator, the collection device, through rubbing or other interactions, accumulates cells or other materials from the lumen to be used for microscope cytology or other analysis.

A collection sponge may be incorporated anywhere on the present invention where it is likely to come in contact with the tissue of interest. For example, it might be included as part of the main tether, the capsule or both. It may be as described in FIG. 9 and FIG. 10, but be affixed permanently to the imaging capsule.

When retrieving the device after images have been acquired of the gastro-esophageal junction or other deep anatomy, the palatant is no longer needed, and its excess diameter becomes an impediment to retrieval of the device. In one embodiment, the palatant slips off in the presence of force exceeding some threshold. While some operator skill can prevent this force from building up as the capsule is positioned, once the operator begins to retrieve the device, it is necessary for the palatant to detach and fall away or disintegrate. In one embodiment, the operator uses a quick, firm pull on the tether to release the device from the capsule. This can be timed with instances when the esophageal musculature is constricting about the capsule, preventing it from being pulled out. To achieve the high force, the pull must be of short duration, and for this short duration force to be transmitted down the length of the tether, the tether may be designed to have minimal longitudinal compliance.

To reduce longitudinal compliance, and increase the strength of the tether, a filament of high tensile strength yet inelastic material can be inserted into the length of the cable, Kevlar thread being a suitable material. In the embodiment being illustrated in FIG. 14, the tubular shell 1401 of the imaging capsule, taper 1402 and tether cable jacket 1403 are shown. Internal to the tether cable are wires 1404 and a Kevlar thread 1405. Although Kevlar thread is one suitable embodiment, other materials having high tensile strength, low elasticity and sufficient flexibility may be used. The thread 1405 is attached to a mechanically stable junction point 1406 inside the imaging capsule—in this case a tie-hole that is part of the internal structure 1407. The Kevlar thread thus forms the major high strength linkage between the tether and the imaging capsule and may be anchored proximally at some point that is proximal to where the operator will grasp and pull the tether. The anchor point may be the proximal termination of the tether.

The distal tip of the tether jacket 1403 is inside the taper 1402. Because the main holding strength is provided by the Kevlar thread, the attachment of the tether jacket to the capsule may be of lower strength. In the absence of the Kevlar thread, and without too much effort, it may be pulled out of and become detached from the imaging capsule. While the jacket is in place, a gasket 1408, 1408' or other barrier is used to prevent water ingress along the tether jacket.

While in some embodiments the device is prevented from detaching from the tether in all circumstances, another set of embodiments allow it to detach intentionally and with the application of sufficient force along the tether by the operator. Various approaches may be used to achieve this result, as exemplified by the design in FIG. 15A.

When the operator has decided to retrieve the device, it may or may not meet with resistance from the esophageal constriction. If not, the device will retrieve easily. If it does meet with resistance, the operator may then have the option to provide a sharp tug on the device, transmitting a high but short-duration force that breaks a critical coupling link and allows the device to slide off. The operator then pulls the tether from the patient, as the capsule slides down into the stomach.

The break-away mechanism may use a short section of line or other member of relatively low tensile strength to serve as the weakest link between the cable and the capsule. As noted above, to transmit a sharp pull along the tether down to the capsule, it is important for the tether compliance to be low, and this may be achieved with Kevlar thread or other strong, non-compliant structure. The force is transmitted to the critical linkage, which forms the "weak link" keeping the imaging capsule connected to the tether. When the critical linkage breaks, other forces that might connect the imaging capsule to the tether fail. For example, the external tether jacket might slip away from the imaging capsule to which it is held by a relatively weak but water-tight bond. Electrical wires within the tether cable should be chosen so as to also break; wires in the 38 AWG range or smaller diameter have been found to be suitable.

In the embodiment shown in FIG. 15A, a distal segment of Kevlar thread 1501 is attached to a much thinner linkage 1502. The linkage 1502 is anchored to a stable connection point 1503 of some internal part 1504 of the imaging capsule. As an example, the full length of the tether may include a 2-4 lb test Kevlar line, terminating in a short length (perhaps 5 mm or less) of thinner weaker line of controlled tensile strength, thus forming a critical link. Strength of the critical link, for example, might be fixed in the range of 1-8 ounces. Other constituents of the cable such as copper wires may be chosen to be so fine as to be easily broken once the critical link breaks. The tether cable jacket may be designed to initially form a water-tight seal with the imaging capsule, but to later easily slip away from the capsule. For example, silicone RTV may provide both the weak bond and the seal for the jacket. Additionally, as shown in FIG. 15B, at least one of the fine copper wires 1555 (in range of 40-50 AWG, for example) along with a return line 1557 may provide a means to monitor real time the structural integrity of the assembly attachment by providing an electrical continuity loop. A member 1559 joining the copper wire 1555 and the return line 1557 is configured such that the wires are disconnected in response to operation of the tether. When the continuity loop is disrupted, the controller can immediately shut off all electrical power.

Various other means may be used to achieve the "weak link" such as using two mating magnets, a magnet and a ferromagnetic element, suction cup, ball and socket and many other mechanical approaches. The idea however is the same, namely that the operator can use a sharp tug to disrupt the weak link when the device is impeded by anatomical obstruction.

While means based on direct operator manipulation to achieve disconnection of the imaging capsule as described above are simple and highly reliability, other means are possible including the application of high currents to melt a critical linkage. In one embodiment, a high resistance conductor may be made to break due to heating effects from an electric current, the conductor serving as the critical linkage. Alternatively, the heat may weaken or melt another material (such as a polymer) that is in close proximity and forms the critical linkage.

Two attracting magnets (e.g. strong rare-earth) or a magnet and a ferromagnetic lump of metal can be used to create the critical link attachment. At least one of the magnets may be an electromagnet.

Weight may be added to the capsule and related structures to allow gravity to pull the imaging capsule through the lumen. FIG. 16 shows a taper that integrates with an imaging capsule 1601 and its tether 1602. A circularly symmetric set of beads 1603, 1604 and 1605 each have a small diameter lumen large enough to accommodate the tether 1602. The beads, when collapsed, form a continuous, cylindrically symmetrical taper. By allowing the beads to slide along their flat contacting surfaces flexibility can be simulated in a "piecewise" manner. Of course, more or fewer beads can be used, and they may be joined together and to the imaging capsule by a very flexible substrate allowing the taper so formed to bend. One embodiment uses tungsten beads. Protruding edges in such a design may be a problem, as they may enable constricting musculature to better grip the device and prevent its retrieval. To mitigate this problem, the sharp edges of the beads may be replaced with rounded or blunted transitions. The beads may be encased or covered in a substrate, taking on the external form of the taper 12 in FIG. 1A. In this case, the beads are hidden with the external substrate, which might be silicone rubber or another polymer. Distal beads, such as 1603, may not be tapered, instead being cylindrical to match the diameter of imaging capsule 1601. In one case, bead 1603 may be attached and made integral to the imaging capsule 1601.

In one embodiment, one or more weights are arranged to slide along the tether line, much like fishing weights that each has a single hole. The weights may be withheld during the introduction of the capsule into the esophagus, after which each weight can be inserted into the oral cavity, allowing the patient to swallow it. To make it palatable, the weight can include or be coated with palatable material such as those previously described.

A taper 1702 as shown in FIG. 17 may comprise a flexible substrate such as silicone rubber that may be "doped" with heavy solid particles. Illustrative embodiments use tungsten particles such as beads or powder, as tungsten is extremely dense (19 g/ml) and non-toxic. In addition, the taper 1702 has a proximal portion 1704 and a distal portion 1706. Within the proximal portion is provided a metallic or other high-density body 1708. The distal portion 1706 is flexible and elongated. For example, the distal portion 1706 may be two or more times as long as the proximal portion, enhancing the wedge effect of the taper. The distal portion 1706 may be doped with metallic particles. The taper may be made more flexible by adding slits to the taper.

In other embodiments, the entire taper might be made of high density material, even to the point of being able to slide up and down the tether. Tungsten fashioned in the manner of fishing weights having centrally located longitudinal holes, and with conical, spindle or other forms may be used for this purpose.

Experiments suggest that as little as even 1 gram of extra weight may significantly improve the gravity effects. As an example, an imaging capsule may be 4 mm diameter. A taper extending proximally (toward the mouth, away from the stomach) may be conical with a distal base of 4 mm diameter and about 15 mm long. This taper may therefore have about 0.06 ml volume. With tungsten being about 19 g/ml in density, a fill of about 80% by volume of the taper would yield 1 gram added weight from the tungsten.

Other weight adding materials can be used, such as stainless steel, copper, bronze, brass, etc., which have densities in or near the 7-8 $g/cm^3$ range. Tungsten and gold are examples of very dense, heavy metals that are non-toxic, tungsten being relatively more affordable.

The present esophageal probe, in its various embodiments, is inexpensive and may be used without extensive training. The various features described enhance the effectiveness of the probe and increase patient comfort. Taken together, these features make the esophageal probe attractive for use by physicians and their staff, enabling important screening procedures to be performed routinely and affordably.

It will be appreciated by those skilled in the art that the present invention may be embodied in other specific forms without departing from the spirit or essential character thereof. The foregoing description is therefore intended in all respects to be illustrative and not restrictive. The scope of the invention is indicated by the following claims, not the foregoing description, and all changes which come with the meaning and range of equivalents thereof are intended to be embraced therein.

What is claimed is:

1. An esophageal probe system comprising:
   a tethered imaging capsule, the tether configured to provide a pulling force and no pushing force on the imaging capsule; and
   at least one swallowing aid configured to be removably or temporarily attached to the tethered imaging capsule, configured to be swallowed with the tethered imaging capsule, and constructed to make ingestion easier when ingested orally;
   wherein the swallowing aid detaches distally from the tethered imaging capsule by operation of a primary tether coupled to the tethered imaging capsule.

2. The esophageal probe system of claim 1, wherein the swallowing aid comprises one or more alignment features configured to align an axis of the imaging capsule with an axis of a patient's esophagus.

3. The esophageal probe system of claim 2, wherein the one or more alignment features comprise a plurality of fins.

4. The esophageal probe of claim 1, wherein the swallowing aid is tethered to the imaging capsule by at least one secondary tether.

5. The esophageal probe of claim 1, wherein the primary tether comprises a component having low longitudinal compliance.

6. The esophageal probe of claim 1, wherein the swallowing aid is flavored.

7. The esophageal probe of claim 1, wherein the swallowing aid is scented to enhance palatability.

8. The esophageal probe of claim 1, wherein the swallowing aid is provided with a tactile property to enhance palatability.

9. The esophageal probe system of claim 1, wherein the swallowing aid is constructed with sensory properties including at least one of tactile properties, taste properties, or smell properties that enable the esophageal probe to be more easily ingested.

10. The esophageal probe system of claim 1, wherein the swallowing aid is constructed of a digestible material.

11. The esophageal probe system of claim 10, wherein the digestible material comprises hydrocolloid.

12. The esophageal probe system of claim 1, wherein the swallowing aid is constructed of non-digestible material.

13. The esophageal probe system of claim 12, wherein the non-digestible material comprises low-durometer silicone elastomer material.

14. The esophageal probe system of claim 1, wherein the swallowing aid is shaped to enable peristaltic action to be more effective in propelling the esophageal probe system downward through an esophagus.

15. The esophageal probe system of claim 1, wherein the swallowing aid comprises added weight to assist in a decent of the esophageal probe system through an esophagus.

16. The esophageal probe system of claim 1, wherein the operation of the primary tether to detach the swallowing aid comprises a mechanical force including at least one of a controlled upward force, an operator applied upward force, or a sharp tug.

17. A method of administering an esophageal exam to a patient, comprising:
    attaching a swallowing aid to a tethered imaging capsule to form an esophageal probe;
    wherein the swallowing aid is configured to be removably or temporarily attached to the tethered imaging capsule, configured to be swallowed with the tethered imaging capsule, and constructed to make ingestion easier when ingested orally;
    and
    causing the patient to swallow the esophageal probe, wherein removal of the swallowing aid comprises distally detaching the removable swallowing aid from the tethered imaging capsule by operation of a primary tether coupled to the tethered imaging capsule, which provides a pulling force and no pushing force on the imaging capsule.

18. The method of claim 17, further comprising:
    causing removal of the swallowing aid; and
    withdrawing the tethered imaging capsule from the patient's esophagus.

19. The method of claim 17, wherein removal of the removable swallowing aid comprises an operator operating the tether of the tethered imaging capsule.

20. The method of claim 17, comprising:
    texturing the swallowing aid prior to causing the patient to swallow the esophageal probe to enhance palatability.

21. The method of claim 17, comprising:
    coloring the swallowing aid prior to causing the patient to swallow the esophageal probe to enhance palatability.

22. The method of claim 17, wherein the swallowing aid comprises agar.

23. The method of claim 17, wherein the swallowing aid comprises silicone.

24. The method of claim 17, wherein the swallowing aid comprises a material that dissolves or melts during swallowing.

25. The method of claim 17, wherein the swallowing aid comprises hydrocolloid.

26. The method of claim 17, comprising coating the esophageal probe prior to causing the patient to swallow the esophageal probe.

27. The method of claim 26, wherein the coating provides low friction properties and enhances palatability.

* * * * *